United States Patent [19]

Kakarla et al.

[11] Patent Number: 5,731,423
[45] Date of Patent: Mar. 24, 1998

[54] PROCESS FOR PREPARING SULFOXIDES

[75] Inventors: Ramesh Kakarla, East Brunswick; Michael J. Sofia, Lawrenceville, both of N.J.

[73] Assignee: Transcell Technologies, Inc., Monmouth Junction, N.J.

[21] Appl. No.: 619,170

[22] Filed: Mar. 21, 1996

[51] Int. Cl.$^6$ .................................................. C07G 3/00
[52] U.S. Cl. ........................................................ 536/4.1
[58] Field of Search ............................. 536/6, 18.5, 4.1

[56] References Cited

U.S. PATENT DOCUMENTS 5,442,058  8/1995  Nieuwenhuis ........................... 540/314

OTHER PUBLICATIONS

Carbohydrate Research 58 (1977) 397–404, Ferrier et al. "Observations on Possible Application of glycosyl disulphides, Sulphenic Esters, and Sulphones in the Synthesis of Glycosides".
Field, Lamar, *Some Developments in Synthetic Organic Sulfur Chemistry*, 1978, pp. 713–740.
Block, Eric, *Reactions of Organosulfur Compounds*; Academic: New York, 1978 (Book).
Sir Derek Barton, F.R.S. and W. David Ollis, F.R.S., Comprehensive Organic Chemistry—The Synthesis and Reactions of Organic Compounds; vol. 3—*Sulphur, Selenium, Silicon, Boron, Organometallic Compounds*; Pergamon: Oxford, U.K., 1979.
Kahne, Daniel; Walker, Suzanne; Cheng, Yuan; Van Engen, Donna, Glycosylation of Unreactive Substrates; J. Am. Chem. Soc. 1989, 111, p. 6881.
Sliedregt, L.A.J.M.; Van Der Marel, G.A.; Van Boom, J.H., Trimethylsilyl Triflate Mediated Chemoselective Condensation of Arylsulfenyl Glycosides; Tetrahedron Letters 1994, vol. 35, No. 23, pp. 4015–4018.
Zhang, Hong; Wang, Yali; Voelter, Wolfgang, A New Strategy for the Synthesis of the Nephritogenoside Trisaccharide Unit Using Phenylfulfenyl Donors; Tetrahedron Letters 1995, vol. 36, No. 8, pp. 1243–1246.
Wang, Yali; Zhang, Hong; Voelter, Wolfgang, *Block Synthesis of Oligosaccharides under Mild Conditions*; 1995, pp. 661–666.
Khiar, N.; Martin–Lomas, M., A Highly Convergent Synthesis of the Tetragalactose Moiety of the Glycosyl Phosphatidyl Inositol Anchor of the Variant Surface Glycoprotein of *Trypansoma brucei*; J. Org. Chem. 1995, 60, pp. 7017–7021.
Yang, D.; Kim, Soong–Hoon, Kahne, Daniel, *Construction of Glycosidic N–O Linkages in Oligosaccharides*; J. Am. Chem. Soc. 1991, 113, pp. 4715–4716.
Cheng, Yuan; Ho, Douglas M.; Gottlieb, Craig R.; Kahne, Daniel; Bruck, Michael A., Facial Amphiphiles; J. Am. Chem. Soc. 1992, 114, p. 7319.
Kahne, Daniel; Raghavan, Subharekha, A One–Step Synthesis of the ciclamycin Trisaccharide; J. Am. Chem. Soc. 1993, 115, p. 1580.

Allanson, Nigen; Chan, Tin Yau; Chen, Anna; Chen, Ru; Liu, Dashan; Baizmen, Eugene; Mintz, Clifford; Axelrod, Helena; Sofia, Michael J., The Design and Construction of a Combinatorial Glycopeptide Library to Identify Potential Antibacterial Agents; Abst. #199 (Div. of Med. Chem.), 211th ACS National Meeting, New Orleans, 1996.
Patai, Saul; Rapporport, Zvi, Eds.; *The syntheses of sulphones, sulphoxides and cyclic sulphides*; John Wiley and Sons: Chichester, U.K., 1994.
Uemura, Sakae; 6.2 *Oxidation of Sulfur, Selenium and Tellurium*; Kyoto University, Japan, vol. 7, Ley. S.,V. Ed.; Pergman: Oxford, 1991, 757–787.
Fabretti, Antonio; Ghelfi, Franco; Grandi, Romano; Pagnoni, Ugo M.; Sulfoxides From Thioethers and MnO$_2$–HCl; Synth. Comm. 1994, 24, pp. 2393–2398.
Siedlecka, Renata; Skarzewski, Jacek; Facile Oxidation of Sulfides to Sulfoxides using Sodium Hypochlorite and Oxoammonium Salt as a Catalyst: Chemo– and Diastereoselective Transformation of Bis(phenylthio) alkanes into Sulfoxides; Synthesis, Apr. 1994, pp. 401–404.
DesMarteau, Darryl D.; Petrov, Viacheslav A.; Montanari, Vittorio; Pregnolato, Massimo; Resnati, Giuseppe, Mild and Selective Oxygenation of Sulfides to Sulfoxides and Sulfones by Perfluoro–cis–2,3–dialkyloxaziridines; J. Org. Chem., 1994, 59, pp. 2762–2765.
Adam, Waldemar; Mitchell, Catherin M.; Saha–Moller, Chantu R.; Chemoselective Methyltrioxorhemium (VII)—Catalyzed Sulfoxidations with Hydrogen Peroxide; Tetrahedron 1994, vol. 50, No. 46, pp. 13121–13124.
Breton, Gary W.; Fields, John D.; Kropp, Paul J., *Surface–Mediated Reactions. 5. Oxidation of Sulfides, Sulfoxide, and Alkenes with tert–Butyl Hydroperoxide*[1]; Tetrahedron Lett. 1995, vol. 36, No. 22, pp. 3825–3828.
Orito, Kazukhko; Hatakeyama, Takahiro; Mitsuhiro; Suginome, Hiroshi; Oxidation with Mercury (II) Oxide–Iodine Reagent:Selective Oxidation of Sulfides to Sulfoxides; Synthesis, Nov. 1995, pp. 1357–1358.
Aldea, Raluca; Alper, Howard, Selective Aerobic Oxidation of Sulfides Using a Novel Palladium Complex as the Catalyst Precursor; J. Org. Chem., 1995, 60, pp. 8365–8366.
Balicki, Roman; Kaczmarek, Lukasz; Nantki–Namirsi, Pawel; A Mild and Facile Preparation of Sulfoxides from Sulfides by Use of the H$_2$O$_2$–Urea/Phthalic Anhydride System; Liebigs Ann. Chem. 1992, pp. 883–884.
Yan, Lin; Taylor, Carol M.; Goodnow, Jr., Robert; Kahne, Daniel, Glycosylation on the Merrifield Resin Using Anomeric Sulfoxies; J. Am. Chem. Soc. 1994, 116, 6953.

(List continued on next page.)

*Primary Examiner*—C. Warren Ivy
*Assistant Examiner*—Jean F. Vollano
*Attorney, Agent, or Firm*—Lowe, Price, LeBlanc & Becker

[57] ABSTRACT

A process is disclosed for making a compound having a sulfoxide group comprising providing a first compound having a sulfide group and contacting said first compound with an oxidizing agent in the presence of silica and a carboxylic acid anhydride. In a particular embodiment of the invention, the high yield preparation of glycoside moieties having anomeric sulfoxides at ambient temperature is described.

22 Claims, No Drawings

OTHER PUBLICATIONS

Kim, Soong–Hoon; Augeri, David; Yang, Dan; Kahne, Daniel, Concise Synthesis of the Calicheamicin Oligosaccharide Using the Sulfoxide Glycosylation Method; J. Am. Chem. Soc. 1994, 116, pp. 1766–1775.

Walker, Suzanne; Sofia, Michael, J.; Kakarla, Ramesh; Kogan, Natan A.; Wierichs, Leigh; Longley, Clifford B.; Bruker, Karen; Axelrod, Helen R.; Midha, Sunita; Babu, Suresh; Kahne, Daniel; Cationic facial amphiphiles: A promising class of transfection agents; Proc. Natl. Acad. Sci., vol. 93, pp. 1585–1590.

Walker, Suzanne; Kahne; Dissertation—Part 1. Glycosylation Using Anomeric Sulfoxides. Part 2. Calicheamicin Studies on the Structure and Function of Oligosaccharide Tail; Princeton University, Jan. 1992 pp. 1–156.

Schmidt, Richard R.; Kast, Jürgen; Direct Lithiation of Glycals. Synthesis of C–2 Branched Sugars; Tetrahedron Lett. 1986, vol. 27, No. 34, pp. 4007–4010.

Longely, C.; Axelrod, H.R.; Midha, S.; Kakarla, R.; Kogan, N.A.; Sofia, N.J.; Babu, S.; Wierichs, L.; Walker, S., Conjugates of Glycosylated Steroids and Polyamines as Novel Nonviral Gene Delivery Systems; Ann. N.Y. Acad. Sci U.S.A. 1995, pp. 268–270.

Kakarla, Ramesh; Kogan, Natan A.; Dulina, Richard; Hui, Y.W.; Hatzenbuhler, Nicole T.; Liu, Dashan; Chen, Anna; Wagler, Tom; Sofia, Michael J., An Efficient Synthesis of Methyl 3–β–Amino–7α,12α–Dl (1'α–Glucosyl)–5β–Cholate; Abst. #320 (Div. of Org. Chem.) 211th ACS National Meeting, New Orleans, 1996.

Chan, Tin Yau; Chen, Anna; Allanson, Nigel; Chen, Ru; Liu, Dashan; Sofia, Michael J., Solid Supported Glycopeptide Synthesis for the Construction of A Glycopeptide Combinatorial Library; Abst. #198 (Div. of Med. Chem.), 211th ACS National Meeting, New Orleans, 1996.

Karkala, R.; Dulina, R.G.; Hatzenbuhler, N.T.; Hui, Y.W., Sofia, M.J.; Simple and Efficient Method for the Oxidation of Sulfides to Sulfoxides: Application to the Preparation of Glycosyl Sulfoxides, J. Org. Chem., Nov. 1996, vol. 61, No. 23, pp. 8347–8349, especially results and discussion section 8347 and 8348.

Ko, S.Y.; Lee, A.W.M; Masamune, S., Reed, III, L.A.; Sharpless, K.B.; Walker, F.J.: Total Synthesis of the L–Hexoses, Tetrahedron, Jan. 1990, vol. 46, No. 1, pp. 245–264, especially p. 251 second paragraph.

Samanen, J.M., Brandeis, E.; The p–(Methysulfinyl)benzyl Group: A TFA–Stable Carboxyl–Protecting Group Readily Convertible to a TFA–Labile Group, J. Org. Chem., Jan. 1988, vol. 53, No. 3, pp. 561–569, especially p. 563 scheme II.

Database Casreact on STN, Pharm. Institute, University of Bonn (Bonn, Ger) No. 105:42575, Lehmann, J. et al. 'Lactones. vol. III., Reactions of methyl 2–(4–chlorophenoxy)–, 2–[4–chlorophenyl)thio]–and 2–[(4–chlorophenyl) sulfinyl] propionates with oxirane.' abstract, Arch Pharm. (Weinheim, Ger), 319(3), Aug. 1986, see entire abstract.

5,731,423

1
PROCESS FOR PREPARING SULFOXIDES

FIELD OF THE INVENTION

The present invention relates generally to a process of making sulfoxides. More particularly, the present invention relates to a process of making a compound having a sulfoxide group comprising providing a first compound having a sulfide group and contacting the first compound with an oxidizing agent in the presence of an adsorbent and a carboxylic acid anhydride. In a preferred embodiment, glycosides having an anomeric sulfoxide group are made from the corresponding glycoside having an anomeric sulfide group.

The present invention takes advantage of the discovery of a simple and efficient process for oxidizing a sulfide group to a sulfoxide group under mild conditions with minimal, if any, over oxidation to the corresponding sulfone. The process of the present invention is suitable for large-scale production of virtually any sulfoxide group-containing compound, including such complex molecules as glycosidic sulfoxides and the like.

BACKGROUND OF THE INVENTION

Compounds containing sulfoxide groups are known to be useful synthetic intermediates for the construction of a large variety of chemically and biologically significant molecules. See, e.g., Field, L., in *Synthesis* (1978):713; Block, E., in *Reactions of Organosulfur Compounds*, Academic Press (New York) 1978; Durst, T., in *Comprehensive Organic Chemistry*, Barton, D. and Ollis, W. D., Eds., Vol. 3, Pergamon Press (Oxford) 1979. A new method for glycosylation involving anomeric sugar sulfoxides was reported by Kahne and co-workers. See, Kahne, D. E. et al., in *J. Am. Chem. Soc.* (1989) 111:6881. In the reported method, anomeric sugar sulfides were oxidized using m-chloroperoxybenzoic acid (mCPBA) in methylene chloride at very low temperatures.

The oxidation of sulfides to sulfoxides or sulfones has been studied extensively using a variety of protocols. See, e.g., Patai et al., Eds. *The Chemistry of Sulphones, Sulphoxides and Cyclic Sulphides*, John Wiley and Sons (Chichester, U.K.) 1994; Uemura, S., in *Comprehensive Organic Synthesis*, Vol. 7, Ley, S. V. (Ed.) Pergamon Press (Oxford) 1991. p. 757; Fabretti et al., in *Synth. Comm.* (1994) 24:2393; Siedlecka et al., in *Synthesis* (1994):401; Desmartean et al., in *J. Org. Chem.* (1994) 59:2762; Adam et al., in *Tetrahedron* (1994) 50:13121; Breton et al., in *Tetrahedron Lett.* (1995) 36:3825; Orito et al., in *Synthesis* (1995):1357; and Aldea et al., in *J. Org. Chem.* (1995) 60:8365.

The oxidation of glycosylsulfides to sulfoxides using mCPBA has its drawbacks. For example, oxidation with mCPBA must be initiated at −78° C. to avoid over oxidation to the sulfone. The reaction mixture must then be warmed slowly to −30° C. to complete the reaction. Further, mCPBA is poorly soluble in dichloromethane, and the complete removal of m-chlorobenzoic acid (the spent oxidant) from the reaction mixture is difficult and often unachievable. Moreover, over oxidation to the sulfone is sometimes observed even in the course of workup at room temperature.

Thus, the state of the art underscores the prevailing and unfulfilled need for the ready and convenient conversion of a compound having a sulfide group to a compound having a sulfoxide group. In particular, a process for oxidizing a glycosidic sulfide to its corresponding glycosidic sulfoxide at ambient temperature would be a substantial contribution to the art and would facilitate the large-scale production of complex sulfoxides.

2
SUMMARY OF THE INVENTION

The present invention provides processes of making a compound having a sulfoxide group. The compounds that can be made by the process of the present invention include any organic compound that contains at least one sulfinyl group, —S—, covalently bonded to two carbon atoms.

The present invention is based on the discovery that when a compound having a sulfide group is contacted with an oxidizing agent in the presence of an adsorbent and a carboxylic acid anhydride, excellent yields of the corresponding sulfoxide are obtained under mild conditions, typically at ambient temperature. Furthermore, the conversion is observed with little or no unwanted over oxidation to the sulfone. A preferred embodiment of this invention involves the synthesis of glycosides having an anomeric sulfoxide group by contacting a glycosidic sulfide with an oxidizing agent, such as hydrogen peroxide, in the presence of silica gel and an anhydride, such as acetic anhydride.

Accordingly, it is an object of the invention to provide a high yield process for the preparation of sulfoxides at ambient temperature.

It is also an object of the invention to provide a large scale process for the preparation of sulfoxide-containing compounds from the corresponding sulfides. Such a process will preferably not require low temperature conditions.

It should be apparent that the present invention provides a process of oxidizing a sulfide group to a sulfoxide group comprising contacting a sulfide group with an oxidizing agent in the presence of an adsorbent and a carboxylic acid anhydride.

These and other objects of the present invention will become apparent to those of ordinary skill in the art on consideration of the present disclosure.

DETAILED DESCRIPTION OF THE INVENTION

What follows is a detailed description of the preferred embodiments of the present invention.

The present invention relates to a process of making a sulfoxide comprising providing a sulfide and contacting the sulfide with an oxidizing agent in the presence of an adsorbent and a carboxylic acid anhydride to provide a reaction mixture containing a sulfoxide. In a particular embodiment of the present invention, the process further comprises recovering the sulfoxide from the reaction mixture in substantially pure form. In still other embodiments, the process further comprises filtering the reaction mixture, washing the filtered reaction and removing any volatile components. Preferably, the sulfide is contacted with an oxidizing agent in the presence of a carboxylic acid anhydride and a solvent, followed by the addition of an adsorbent.

In the process of the invention the oxidizing agent is preferably present in a stoichiometric amount or a slight excess while the carboxylic acid anhydride is preferably present in a stoichiometric amount or a slight excess. The adsorbent should be present in an amount effective to be a catalyst (a "catalytic" amount), typically in a catalytic amount on a weight basis versus the amount of starting sulfide used.

The process can be carried out under a variety of reaction conditions, including a wide range of temperatures or periods of reaction. However, the process is most adventitious and convenient when conducted at or near ambient temperature and for an overnight period.

Further, in the present invention the starting sulfide either is free of interfering functional groups or bears protecting groups for any functional groups present that may interfere with the oxidation of the thio group of the sulfide.

The process proceeds relatively rapidly and, generally, is complete within about 4 to about 30 hours. The process, hence, can be carried out over a period of about 4 to about 30 hours, preferably about 6 to about 24 hours.

In a preferred embodiment of the invention, the disclosed process is carried out to prepare a glycoside having an anomeric sulfoxide group comprising the steps of providing a glycoside having an anomeric sulfide group and contacting the glycoside having an anomeric sulfide group with an oxidizing agent comprising hydrogen peroxide in the presence of silica comprising silica gel and a carboxylic acid anhydride comprising acetic anhydride to provide a reaction mixture containing a glycoside having an anomeric sulfoxide group.

To initiate the reaction, an oxidizing agent is added to a stirred mixture comprising a compound having a sulfide group, a carboxylic acid anhydride, an adsorbent and a solvent at a chosen temperature (e.g., room temperature). The corresponding sulfoxide is recovered in substantially pure form by simply filtering the reaction mixture, washing the filtered reaction mixture, followed by removal of the solvent. Solvents suitable for the present invention include, but are not limited to, methylene chloride, tetrahydrofuran, methanol, ethanol, propanol, ether, acetone, ethyl acetate and the like, including mixtures thereof.

The sulfoxide compounds, which may be prepared according to the present process, include any organic compound that contains at least one sulfinyl group covalently bonded to carbon. Preferably, the sulfur atom is bonded to two carbon atoms.

Linear or branched alkyl, cyclic alkyl, aralkyl, aromatic sulfoxides, or various combinations thereof, are among the many compounds that may be prepared according to the present invention. Preferred sulfoxides are glycosides having an anomeric alkyl or aryl sulfoxide group. The term "glycoside" or "glycosyl" encompasses any sugar containing at least one pentose or hexose residue.

As used herein, the term "carboxylic acid anhydride" refers to any reagent having the functional group —CO—O—CO—, i.e., a condensation product of two carboxylic acids minus a molecule of water. The carboxylic acid anhydride may be a linear, branched, or cyclic aliphatic carboxylic acid anhydride, an aralkyl (or arylaliphatic) carboxylic acid anhydride, or an aromatic carboxylic acid anhydride. Examples of suitable aliphatic carboxylic acids include, but are not limited to, acetic anhydride, propionic anhydride, butyric anhydride, pentanoic anhydride, hexanoic anhydride, octanoic anhydride and decanoic anhydride. Acetic anhydride is a preferred aliphatic carboxylic anhydride. Examples of suitable cyclic carboxylic acid anhydrides include, but are not limited to, succinic anhydride, maleic anhydride and itaconic anhydride. Examples of suitable aromatic carboxylic acid anhydrides include, but are not limited to, benzoic acid anhydride, phthalic acid anhydride and toluic acid anhydride. The useful amounts of carboxylic acid anhydrides can be readily determined by one of ordinary skill in the art. Preferably, however, it is present in about an equimolar to about a slight excess of the amount of starting sulfide.

The term "adsorbent" refers to any material that has the ability to condense or hold molecules of other substances on its surface. Silica is among the adsorbents that are useful in the present invention. Other suitable adsorbents include, but are not limited to alumina, activated magnesium silicates and the like.

The term "silica" denotes the substance silicon dioxide. Noncrystalline forms of silica are preferred herein and include, but are not limited to, silica gels that contain three-dimensional networks of aggregated silica particles of colloidal dimensions. The preferred particle size of the silica gel may range from about 0.015 mm to about 10 mm, more preferably from about 0.04 mm to about 0.07 mm. An example of a preferred silica gel is E. Merck Kieselgel 60™ or EM Science Silica Gel 60™. An example of a preferred activated magnesium silicate is Florisil™. The silica is generally present in excess, preferably in a range of about 10% to about 50% by weight of the amount by weight of starting sulfide, preferably about 15% to about 30% by weight, most preferably about 25% by weight of the amount by weight of starting sulfide. The alumina and activated magnesium silicates may be present in corresponding amounts.

Alternatively, about 50 to about 150 mg, preferably about 100 mg, of silica or other adsorbent can be used for each mmol of starting sulfide. Adjustments to these amounts can, of course, be made as the need arises. An effective amount of the silica in the present invention may be referred to herein as an "adsorbent effective amount."

A variety of oxidizing agents may be used in the present invention. Typically, an oxidizing agent, which increases the oxygen content of an organic molecule, can be used. Examples of oxidizing agents useful in the present invention include, but are not limited to, potassium persulfate, ammonium persulfate, hydrogen peroxide, benzoyl peroxide, di-tert-butyl peroxide, decanoyl peroxide, lauroyl peroxide, perbenzoic acid, peracetic acid, performic acid, monoperphthalic acid and alkylhydroperoxide derivatives. A preferred oxidizing agent is hydrogen peroxide, which is preferably present in an amount that is substantially stoichiometric or equimolar with the amount of starting sulfide. In certain cases, a slight excess of or a limiting amount of the oxidizing agent may be used, as appropriate to the particular characteristics of the starting sulfide. Most preferably, about a 10% to about 20% molar excess of the oxidizing agent is used relative to the molar amount of starting sulfide.

The process of the invention can be carried out over a wide range of temperature. Most conveniently, however, the reaction temperature ranges from about 20° C. to about 50° C. More preferably, the process in conducted at about 30° C. to about 40° C., most preferably from between about 20° C. to about 30° C. Ideally, the process is carried out at ambient or room temperature, that is, at about 25° C. The reaction is generally complete in less than about 30 hours, preferably between about 6 and about 24 hours, more preferably overnight with little or no over oxidation to the sulfone.

In a particular embodiment of the invention, an oxidizing agent, a compound having a sulfide group, a carboxylic acid anhydride and a solvent are combined and stirred at room temperature. To this reaction mixture is then added an adsorbent effective amount of an adsorbent. The desired sulfoxide may be recovered in substantially pure form, e.g., substantially free of sulfone or starting sulfide. Typically, work up involves filtering the reaction mixture and washing the filtered reaction mixture successively with aqueous $NaHSO_3$, $NaHCO_3$ and brine. Any volatile components, usually the solvent, can then be removed (e.g., by evaporation of the solvent under vacuum).

Hence, in a specific embodiment of the invention a reaction mixture comprising starting sulfide (1 mmol), oxidizing agent (1.2 mmol), carboxylic acid anhydride (1.1 mmol) and adsorbent (100 mg, 200–400 mesh) in a nonpolar organic solvent, such as methylene chloride, is stirred at room temperature overnight to provide a desired sulfoxide in over 60% yield, preferably over 80% yield, more preferably over 90% yield, most preferably over 95% yield.

EXAMPLES

The following specific examples are provided to better assist the reader in the various aspects of practicing the invention. As these specific examples are merely illustrative, nothing in the following descriptions should be construed as limiting the invention in any way. Such limitations are, of course, defined solely by the accompanying claims.

Reactions are run at room temperature. ACS grade solvents are used for the reaction. Flash chromatography employs E. Merck silica gel (Kieselgel 60, 230–400 mesh). TLC is performed with 0.2 mm coated commercial silica gel plates (E. Merck, Kieselgel 60 $F_{254}$). Melting points are determined using a Mel-Temp 11 (Laboratory Devices) capillary-melting-point apparatus in open capillary tubes and are uncorrected. Microanalysis are performed by Atlantic Microlab, Inc., Norcross, Ga. Infrared Spectra are recorded on Midac Prospect-IR (FT-IR) and reported in wavenumbers ($cm^{-1}$). Proton NMR spectra are measured at 300 MHz on a Varian instrument. Chemical shifts are reported in ppm downfield from TMS. Mass Spectrometry (FAB) analyses are performed by Mid-Atlantic spectrometry services, Frederick, Md. In the following synthetic examples, benzyl phenyl sulfide, di-isopropyl sulfide and di-n-butyl sulfide are obtained from Aldrich Chemical Company. Ethyl 2,3,4,6-tetra-O-acetyl-1-thio-α-D-mannopyranoside and ethyl 2,3,4-tri-O-benzyl-1-thio-α,β-L-fucopyranoside are obtained from Toronto Research Chemicals, Inc. All other starting sulfides are synthesized according to standard methods.

5.1. Synthesis of Benzyl Phenyl Sulfoxide (1)

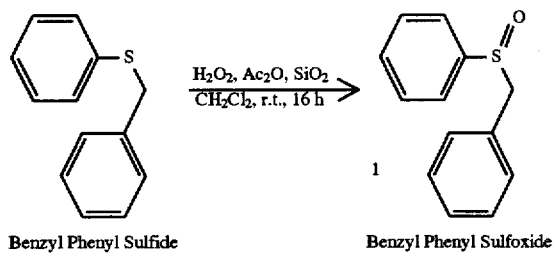

Benzyl Phenyl Sulfide      Benzyl Phenyl Sulfoxide

To a stirred mixture of benzyl phenyl sulfide (1 mmol), acetic anhydride (1.1 mmol) and silica gel (25% by weight to sulfide weight, flash grade, Silica Gel 60, 230–400 mesh) in dichloromethane (20 mL) is added aqueous 30% $H_2O_2$ solution (1.2 mmol). After stirring at room temperature between 2 to 24 h (reaction progress is monitored by TLC), the reaction mixture is filtered and the filtrate washed with saturated aqueous sodium bisulfite (50 mL), sodium bicarbonate (50 mL) and brine (50 mL). The organic layer is separated, dried (anhydrous $Na_2SO_4$) and concentrated to furnish a mixture of the R & S isomers of 1 as a white solid (95% yield after 16 hours, mp 123°–125° C.). TLC $R_f$ (solvent—EtOAc:Hexane=1:4) 0.1. IR (KBr): 3058, 2960, 2910, 1493, 1453, 1442, 1086 and 1035 $cm^{-1}$. $^1H$ NMR ($CDCl_3$): δ 7.46–7.32 (m, 5H), 7.30–7.20 (m, 3H), 7.00–6.80 (m, 2H), 4.03 (q, 4H, $J_1$=17.5Hz, $J_2$=14.0Hz). MS (Fab): 239 (M+Na)$^+$. Anal. Calc. for $C_{13}H_{12}OS$: C, 72.20; H, 5.60; S, 14.80. Found: C, 71.41; H, 5.62; S, 14.66.

5.2. Synthesis Of Di-isopropyl Sulfoxide (2)

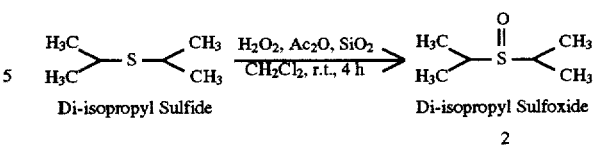

Di-isopropyl Sulfide      Di-isopropyl Sulfoxide

The title compound is prepared from di-isopropyl sulfide by methods similar to those described in Example 1 to furnish a mixture of R & S isomers of 2 as an oil (95% yield after 4 hours). TLC $R_f$ (solvent—EtOAc: Hexane=1:9) 0.1. IR (KBr): 2955, 2927, 2864, 1466, 1453, 1412, 1086 and 1020 $cm^{-1}$. $^1H$ NMR ($CDCl_3$): δ 2.67–2.48 (m, 4H), 1.80–1.68 (m, 4H), 1.58–1.38(m, 4H), 0.95 (t, 3H, $J_1$=7.2Hz). MS (Fab): 157 (M+Na)$^+$. Anal. Calc. for $C_6H_{14}OS$: C, 53.70; H, 10.52; S, 23.85. Found: C, 51.67; H, 10.46; S, 22.81.

5.3. Synthesis Of Di-n-butyl Sulfoxide (3)

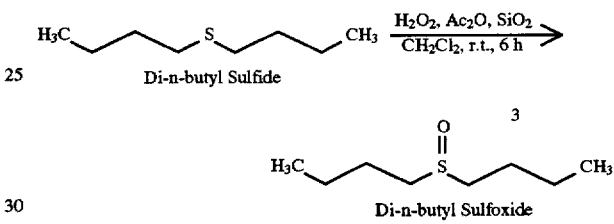

Di-n-butyl Sulfoxide

The title compound is prepared from di-n-butyl sulfide by methods similar to those described in Example 1 to furnish a mixture of R & S isomers of 3 as an oil (95% yield after 6 hours). TLC $R_f$ (solvent—EtOAc:Hexane=1:4) 0.1. IR (KBr): 2968, 2933, 2871, 1462, 1453, 1383, 1366, 1051 and 1012 $cm^{-1}$. $^1H$ NMR ($CDCl_3$): δ 2.81–2.63 (m, 2H), 1.25–1.19 (m, 12H). MS (Fab): 185 (M+Na)$^+$. Anal. Calc. for $C_8H_{18}OS$: C, 59.22; H, 11.19; S, 19.72. Found: C, 57.99; H, 11.16; S, 19.24.

5.4. Synthesis Of Ethylsulphenyl 2,3,4,6-Tetra-O-acetyl-α-D-mannopyranoside (4)

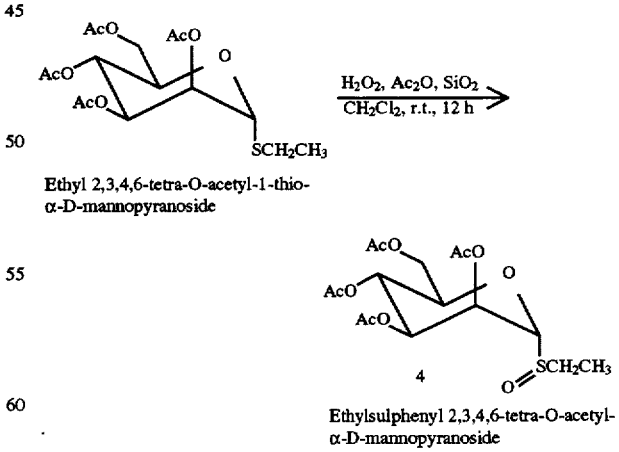

Ethyl 2,3,4,6-tetra-O-acetyl-1-thio-α-D-mannopyranoside

Ethylsulphenyl 2,3,4,6-tetra-O-acetyl-α-D-mannopyranoside

The title compound is prepared from ethyl 2,3,4,6-tetra-O-acetyl-1-thio-α-D-mannopyranoside by methods similar to those described in Example 1 to furnish a mixture of R & S isomers of 4 as a white solid (95% yield after 12 hours, mp 134°–136° C.). TLC R_f (solvent—EtOAc:Hexane=1:2) 0.2. IR (KBr): 2982, 2941, 1746, 1433, 1372, 1250, 1140, 1046 cm⁻¹. ¹H NMR (CDCl₃): δ 5.80 (m, 1H), 5.56 (m, 1H), 4.63 (brs, 1H), 4.32–4.02 (m, 3H), 3.10–2.76 (m, 2H), 2.20–1.94 (m, 12H), 1.42–1.32 (m, 3H). MS (Fab): 431 (M+Na)⁺. Anal. Calc. for $C_{16}H_{24}O_9S$: C, 47.05; H, 5.93; S, 7.83. Found: C, 47.16; H, 5.97; S, 7.73.

5.5. Synthesis Of Phenylsulphenyl 2-Deoxy-2-thalimido-3,4,6-tri-O-acetyl-β-D-glucopyranoside (5)

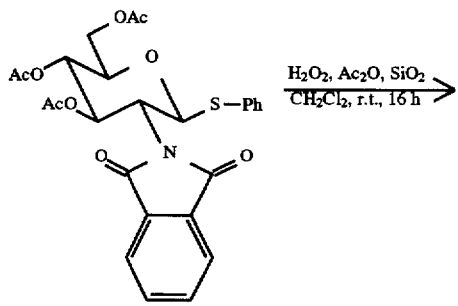

Phenyl 2-deoxy-2-thalimido-3,4,6-tri--O-acetyl-1-thio-β-D-glucopyranoside

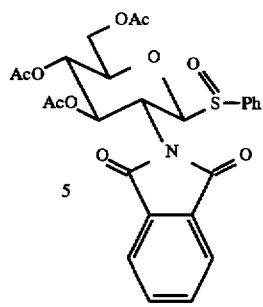

Phenylsulphenyl 2-deoxy-2-thalimido-3,4,6-tri-O-acetyl-β-D-glucopyranoside

The title compound is prepared from phenyl 2-deoxy-2-thalimido-3,4,6-tri-O-acetyl-1-thio-β-D-glucopyranoside by methods similar to those described above in Example 1 to furnish a mixture of R & S isomers of 5 as white solid (82% yield after 24 hours, mp 78°–80° C.). TLC R_f (solvent—EtOAc:Hexane=2:1) 0.3. IR (KBr): 2947, 1749, 1720, 1437, 1379, 1227, 1087 and 1046 cm⁻¹. ¹H NMR (CDCl₃): δ 7.90–7.10 (m, 9H), 5.85–5.70 (m, 1H), 5.50–5.40 (m, 1H), 5.20–4.60 (m, 2H), 4.30–3.80 (m, 3H), 2.20–1.80 (m, 9H). MS (Fab): 566 (M+Na)⁺. Anal. Calc. for $C_{26}H_{25}NO_{10}S$: C, 57.45; H, 4.64; N, 2.58; S, 5.89. Found: C, 55.73; H, 4.55; N, 2.53; S, 5.68.

5.6. Synthesis Of Phenylsulphenyl 2,3,4,6-Tetra-O-acetyl-β-D-glucopyranoside (6)

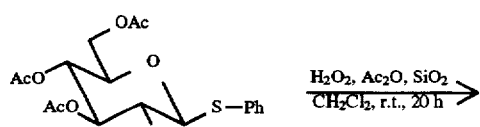

Phenyl 2,3,4,6-tetra-O-acetyl-1-thio-β-D-glucopyranoside

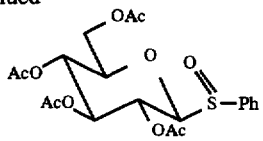

Phenylsulphenyl 2,3,4,6-tetra-O-acetyl-β-D-glucopyranoside 6

The title compound is prepared from phenyl 2,3,4,6-tetra-O-acetyl-1-thio-β-D-glucopyranoside by methods similar to those described above in Example 1 to furnish a mixture of R & S isomers of 6 as a white solid (96% yield after 20 hours, mp 54°–56° C.). TLC R_f (solvent—EtOAc:Hexane=1:1) 0.2. IR (KBr): 2951, 1755, 1746, 1443, 1370, 1229, 1087 and 1041 cm⁻¹. ¹H NMR (CDCl₃): δ 7.65–7.45 (m, 5H), 5.85–5.70 (m, 1H), 5.38–5.18 (m, 2H), 5.04–4.92 (m, 1H), 4.46–3.98 (m, 3H), 3.76–3.56 (m, 1H), 2.10–1.90 (m, 12H). MS (Fab): 479 (M+Na)⁺. Anal. Calc. for $C_{20}H_{24}O_{10}S$: C, 52.62; H, 5.30; S, 7.01. Found: C, 52.43; H, 5.29; S, 6.98.

5.7. Synthesis Of Phenylsulphenyl 2,3,4,6-Tetra-O-pivaloyl-β-D-glucopyranoside (7)

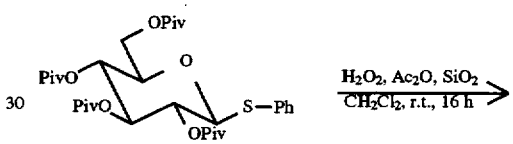

Phenyl 2,3,4,6-tetra-O-pivaloyl-1-thio-β-D-glucopyranoside

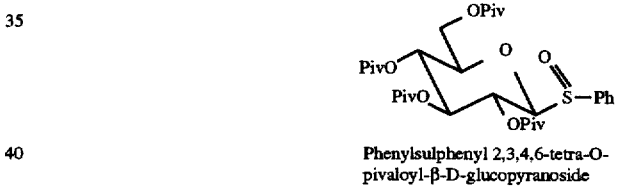

Phenylsulphenyl 2,3,4,6-tetra-O-pivaloyl-β-D-glucopyranoside
7

The title compound is prepared from phenyl 2,3,4,6-tetra-O-pivaloyl-1-thio-β-D-glucopyranoside by methods similar to those described in Example 1 to furnish a mixture of R & S isomers of 7 as a white solid (96% yield after 16 hours, mp 63°–65° C.). TLC R_f (solvent—EtOAc:Hexane=1:3) 0.5. IR (KBr): 2975, 1744, 1480, 1281 and 1150 cm⁻¹. ¹H NMR (CDCl₃): δ 7.69–7.43 (m, 5H), 5.85–5.70 (m, 1H), 5.48–5.30 (m, 1H), 5.06–4.84 (m, 1H), 4.56–3.56 (m, 5H), 1.25–1.05 (m, 36H). MS (Fab): 647 (M+Na)⁺. Anal. Calc. for $C_{32}H_{48}O_{10}S$: C, 61.51; H, 7.75; S, 5.12. Found: C, 61.53; H, 7.79; S, 5.04.

5.8. Synthesis Of Phenylsulphenyl 2-Deoxy-2-azido-4,6-O-benzylidene-β-D-glucopyranoside (8)

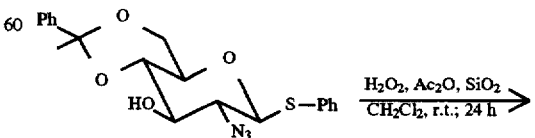

Phenyl 2-deoxy-2-azido-4,6-benzylidene-1-thio-β-D-glucopyranoside

5.10. Synthesis Of Phenylsulphenyl 2,3,4,6-Tetra-O-benzyl-β-D-glucopyranoside (10)

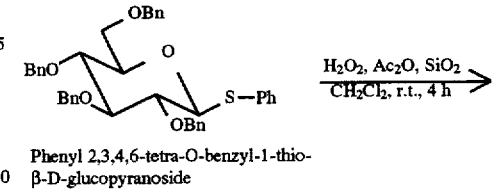

Phenyl 2,3,4,6-tetra-O-benzyl-1-thio-β-D-glucopyranoside

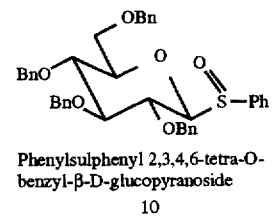

Phenylsulphenyl 2,3,4,6-tetra-O-benzyl-β-D-glucopyranoside
10

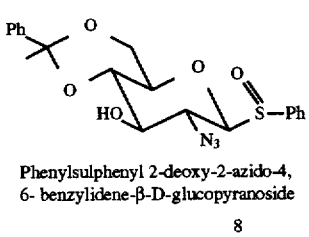

Phenylsulphenyl 2-deoxy-2-azido-4,6-benzylidene-β-D-glucopyranoside
8

The title compound is prepared from 2-deoxy-2-azido-4,6-O-benzylidene-1-thio-β-D-glucopyranoside by methods similar to those described in Example 1 to furnish a mixture of R & S isomers of 8 as a white solid (60% yield after 24 hours, mp 151°–153° C.). TLC $R_f$ (solvent—EtOAc:Hexane=2:3) 0.3. IR (KBr): 3364, 3060, 2974, 2868, 2114, 1480, 1445, 1380, 1267, 1108, 1038 and 1011 cm$^{-1}$. $^1$H NMR (CDCl$_3$): δ 7.76–7.35 (m, 10H), 5.51 (s, 1H), 4.72–4.58 (m, 2H), 4.14–4.00 (m, 2H), 3.98–3.88 (m, 1H), 3.64–3.50 (m, 1H), 3.43 (broad s, 1H). MS (Fab): 424 (M+Na)$^+$. Anal. Calc. for C$_{19}$H$_{19}$N$_3$O$_5$S: C, 56.84; H, 4.77; N, 10.47; S, 7.97. Found: C, 56.34; H, 4.89; N, 10.31; S, 7.87.

The title compounds is prepared from phenyl 2,3,4,6-tetra-O-benzyl-1-thio-β-D-glucopyranoside by methods similar to Example 1 to furnish a mixture of R & S isomers of 10 as a white solid (95% yield after 4 hours, mp 120°–122° C.). TLC $R_f$ (solvent—EtOAc:Hexane=1:3) 0.3. IR (KBr): 3060, 3030, 2910, 2867, 1495, 1450, 1360, 1210, 1136, 1092, 1049 cm$^{-1}$. $^1$H NMR (CDCl$_3$): δ 7.72–7.14 (m, 25H), 5.12–4.42 (m, 9H), 4.40–3.30 (m, 6H). Anal. Calc. for C$_{40}$H$_{40}$O$_6$S: C, 74.04; H, 6.22; S, 4.93. Found: C, 73.96; H, 6.30; S, 4.83.

5.11. Additional Examples Of A Comparative Nature

Additional experiments are conducted to illustrate the benefits of the present invention. For this particular series of experiments, the conversion of phenyl 2,3,4,6-tetra-O-benzyl-1-thio-β-D-glucopyranoside to phenylsulphenyl 2,3,4,6-tetra-O-benzyl-β-D-glucopyranoside (10) is explored under a variety of reaction conditions. The reagents, conditions and results of these experiments are summarized in Table 1, below.

5.9. Synthesis Of Ethylsulphenyl 2,3,4-Tri-O-benzyl-α,β-L-fucopyranoside (9)

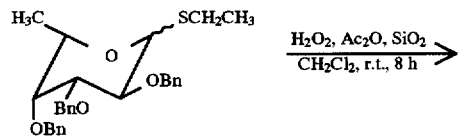

Ethyl 2,3,4-tri-O-benzyl-1-thio-α,β-L-fucopyranoside

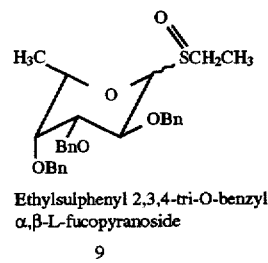

Ethylsulphenyl 2,3,4-tri-O-benzyl-α,β-L-fucopyranoside
9

The title compound is prepared from ethyl 2,3,4-tri-O-benzyl-1-thio-α,β-L-fucopyranoside by methods similar to those described in Example 1 to furnish a mixture of R & S isomers of 9 as an oil (95% yield after 8 hours). TLC $R_f$ (solvent—EtOAc:Hexane=1:2) 0.2. IR (KBr): 3086, 3061, 3029, 2977, 2930, 2872, 1495, 1453, 1358, 1170, 1100, 1066 and 1028 cm$^{-1}$. $^1$H NMR (CDCl$_3$): δ 7.45–7.10 (m, 15H), 5.30–4.60 (m, 7H), 4.35–3.45 (m, 3H), 3.24–3.00 (m, 1H), 1.50–1.00 (m, 8H). MS (Fab): 517 (M+Na)$^+$. Anal. Calc. for C$_{29}$H$_{34}$O$_5$S: C, 70.42; H, 6.93; S, 6.47. Found: C, 69.72; H, 6.86; S, 6.31.

TABLE 1

Preparation of Sulfoxide (10) Under Various Reaction Conditions

| Exp No. | Reagent (mmol) | Solvent (10 mL) | Time (h) | % Yield Sulfoxide | Sulfone | Sulfide |
|---|---|---|---|---|---|---|
| 1$^d$ | mCPBA (1.1) | CH$_2$Cl$_2$ | 2 | 95 | trace | trace |
| 2 | Urea-H$_2$O$_2$ (1.5) | AcOH, THF (2:1) | 72 | 60 | | 40 |
| 3 | Urea-H$_2$O$_2$ (1.5)/ AcOH (2) | CH$_2$Cl$_2$, MeOH (2:1) | 24 | 80 | trace | 20 |
| 4 | Urea-H$_2$O$_2$ (1.5)/ Ac$_2$O (2) | CH$_2$Cl$_2$, MeOH (2:1) | 8 | 85 | 15 | |
| 5* | Urea-H$_2$O$_2$ (1.5)/ AcOH (2) | CH$_2$Cl$_2$, MeOH (4:1) | 96 | 40 | | 60 |
| 6 | (CH$_3$)$_3$CO$_2$H (2)/ AcOH (1) | CH$_2$Cl$_2$ | 48 | 20 | | 80 |
| 7* | (CH$_3$)$_3$CO$_2$H (2)/ AcOH (1) | CH$_2$Cl$_2$ | 48 | 30 | trace | 70 |
| 8* | H$_2$O$_2$ (2) | AcOH, THF (2:1) | 120 | 90 | | 10 |

TABLE 1-continued

Preparation of Sulfoxide (10) Under Various Reaction Conditions

| Exp No. | Reagent (mmol) | Solvent (10 mL) | Time (h) | % Yield[c] Sulfoxide | Sulfone | Sulfide |
|---|---|---|---|---|---|---|
| 9[f] | $H_2O_2$ (4.4) / $CF_3CO_2H$ (1) | THF | 12 | 50 | 10 | 30 |
| 10 | $H_2O_2$ (4.4) / $Ac_2O$ (1) | Acetone | 60 | 90 | trace | 10 |
| 11 | $H_2O_2$ (4.4) / $Ac_2O$ (2) | Acetone | 24 | 85 | 5 | 10 |
| 12[e] | $H_2O_2$ (2.2) / AcOH (2) | $CH_2Cl_2$ | 96 | 40 | | 60 |
| 13[a] | $H_2O_2$ (1.2) / $Ac_2O$ (1.1) | $CH_2Cl_2$ | 4 | 95 | trace | |

[a] 1 mmol of sulfide is used. [b] Mixture of R & S isomers. [c] Isolated yield. [d] Reaction is performed at −78° C. to −30° C. [e] 100 mg of E-Merck silica gel (230–400 mesh) is used as an adsorbent. [f] 10% of unknown compound is also isolated but not characterized.

As evidenced by the results obtained, very good yields of the desired sulfoxide are obtained under a variety of conditions, but significant amounts of over oxidation product begin to be observed under the conditions of Experiment Nos. 4, 9 and 11. In other cases, no significant amount of over oxidation product is observed but the reaction proceeds only sluggishly. Clearly, good results can be obtained at room temperature using slight excess amounts of oxidizing agent and carboxylic acid anhydride. Preferably, the excess amount does not exceed or is less than about 2-fold. More preferably, the about a 5–30% molar excess of each reagent is used relative to starting sulfide, most preferably about a 10–20% molar excess. Good results can also be obtained after a reaction period of less than about 6 hours, preferably about 4 hours.

Other embodiments of the present invention will be evident to one of ordinary skill in view of the detailed description provided herein. Such embodiments are considered to fall within the scope of the present invention, which invention is not limited to the preferred embodiments described above but only by the following claims.

What is claimed is:

1. A process of making a glycoside having an anomeric sulfoxide group comprising (a) providing a glycoside having an anomeric sulfide group and (b) contacting said glycoside having an anomeric sulfide group with an oxidizing agent in the presence of silica and a carboxylic acid anhydride to provide a reaction mixture containing a glycoside having an anomeric sulfoxide group.

2. A process of making a glycoside having an anomeric sulfoxide group comprising (a) providing a glycoside having an anomeric sulfide group and (b) contacting said glycoside having an anomeric sulfide group with an oxidizing agent comprising hydrogen peroxide in the presence of an adsorbent comprising silica gel and a carboxylic acid anhydride comprising acetic anhydride to provide a reaction mixture containing a glycoside having an anomeric sulfoxide group.

3. The process of claim 1 or 2, which further comprises recovering the glycoside having an anomeric sulfoxide group from the reaction mixture in substantially pure form.

4. The process of claim 1 or 2, which further comprises (c) filtering the reaction mixture, (d) washing the filtered reaction and (e) removing any volatile components.

5. The process of claim 1 or 2 in which said glycoside having an anomeric sulfide group is contacted with an oxidizing agent in the presence of a carboxylic acid anhydride and a solvent, followed by the addition of silica.

6. The process of claim 1 or 2 in which the oxidizing agent is present in excess.

7. The process of claim 1 or 2 in which the carboxylic acid anhydride is present in excess.

8. The process of claim 1 or 2, which is carried out at ambient temperature.

9. The process of claim 1 or 2 in which the silica/silica gel has a particle size of from about 0.015 mm to about 10 mm.

10. The process of claim 1 in which the oxidizing agent is selected from the group consisting of potassium persulfate, ammonium persulfate, benzoyl peroxide, hydrogen peroxide, di-tert-butyl peroxide, decanoyl peroxide, lauroyl peroxide, perbenzoic acid, peracetic acid, performic acid, monoperphthalic acid and alkylhydroperoxide derivatives.

11. The process of claim 1 in which the carboxylic acid anhydride comprises an aliphatic carboxylic acid anhydride.

12. The process of claim 11 in which the aliphatic carboxylic acid anhydride is selected from the group consisting of acetic anhydride, propionic anhydride, butyric anhydride, pentanoic anhydride, hexanoic anhydride, octanoic anhydride and decanoic anhydride.

13. The process of claim 1 in which the carboxylic acid anhydride comprises a cyclic carboxylic acid anhydride.

14. The process of claim 13 in which the cyclic carboxylic acid anhydride is selected from the group consisting of succinic anhydride, maleic anhydride and itaconic anhydride.

15. The process of claim 1 in which the carboxylic acid anhydride comprises an aromatic carboxylic acid anhydride.

16. The process of claim 15 in which the aromatic carboxylic acid anhydride is selected from the group consisting of benzoic acid anhydride, phthalic acid anhydride and toluic acid anhydride.

17. The process of claim 1 or 2 which is carried out at a temperature between about 20° to 50° C.

18. The process of claim 17 which is carried out at a temperature between about 20° to 30° C.

19. The process of claim 17 which is carried out at a temperature between about 30° to 40° C.

20. The process of claim 1 or 2 in which said glycoside having an anomeric sulfide group either is free of or bears protecting groups for any functional groups that may interfere with the oxidation of the sulfide group of said glycoside having an anomeric sulfide group.

21. The process of claim 1 or 2 which is carried out over a period of about 4 to about 30 hours.

22. The process of claim 21 which is carried out over a period of about 6 to about 24 hours.

* * * * *